(12) United States Patent
Strassl et al.

(10) Patent No.: US 7,931,645 B2
(45) Date of Patent: Apr. 26, 2011

(54) DENTAL LASER TREATMENT DEVICE

(75) Inventors: Martin Strassl, Salzburg (AT); Anton Kasenbacher, Traunstein (DE)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 1507 days.

(21) Appl. No.: 11/118,304

(22) Filed: Apr. 28, 2005

(65) Prior Publication Data

US 2005/0245917 A1    Nov. 3, 2005

(30) Foreign Application Priority Data

Apr. 28, 2004    (AT) .................................. A 730/2004

(51) Int. Cl.
  *A61B 18/18*    (2006.01)
(52) U.S. Cl. .................. 606/13; 606/10; 606/14; 607/89
(58) Field of Classification Search ........................ None
  See application file for complete search history.

(56) References Cited

U.S. PATENT DOCUMENTS

| | | | | |
|---|---|---|---|---|
| 4,362,057 A | * | 12/1982 | Gottlieb et al. | 374/4 |
| 4,794,619 A | * | 12/1988 | Tregay | 374/131 |
| 5,154,707 A | * | 10/1992 | Rink et al. | 606/12 |
| 5,281,212 A | * | 1/1994 | Savage et al. | 606/15 |
| 5,334,191 A | * | 8/1994 | Poppas et al. | 606/12 |
| 5,409,481 A | | 4/1995 | Poppas et al. | |
| 5,474,449 A | * | 12/1995 | Loge et al. | 433/29 |
| 5,738,678 A | * | 4/1998 | Patel | 606/10 |
| 6,482,199 B1 | * | 11/2002 | Neev | 606/10 |
| 6,676,654 B1 | * | 1/2004 | Balle-Petersen et al. | 606/9 |
| 2001/0025190 A1 | * | 9/2001 | Weber et al. | 607/89 |
| 2002/0013572 A1 | * | 1/2002 | Berlin | 606/4 |
| 2003/0216720 A1 | * | 11/2003 | Sinofsky | 606/11 |
| 2005/0171581 A1 | * | 8/2005 | Connors et al. | 607/88 |

FOREIGN PATENT DOCUMENTS

| | | |
|---|---|---|
| EP | 0 821 907 | 2/1998 |
| EP | 0 864 298 | 9/1998 |
| EP | 0 941 707 | 9/1999 |

OTHER PUBLICATIONS

European Search Report for EPC Patent Application No. 05 00 9295.

* cited by examiner

*Primary Examiner* — Henry M Johnson, III
*Assistant Examiner* — Lynsey Crandall
(74) *Attorney, Agent, or Firm* — Klarquist Sparkman, LLP

(57) ABSTRACT

Described are a handpiece, a coupling, and a device with a laser source and handpiece for emitting a laser beam for dental treatment. In order to avoid damage to the healthy tooth tissue, an improved determination of the tooth temperature by measurement of at least part of the heat radiation emitted from the treatment area using a temperature sensor, preferably an infra-red sensor, is carried out. Upon reaching or exceeding a temperature threshold, the emission of the laser beam to the treatment area is interrupted or the power output of the laser source reduced or the user made aware of the violation of the threshold value using an acoustic or visual signal. The temperature sensor can be located, e.g., on the handpiece or on the coupling, such as on the coupling tube.

22 Claims, 2 Drawing Sheets

DENTAL LASER TREATMENT DEVICE

CROSS-REFERENCE TO RELATED APPLICATION

The present application claims priority from pending Austrian Patent Application No. A 730/2004, filed Apr. 28, 2004, which is incorporated herein by reference.

FIELD

The present invention relates to a handpiece, a coupling and a device with a laser source and handpiece for emitting a laser beam for dental treatment.

DESCRIPTION OF PRIOR ART

The aim of every therapeutic or diagnostic treatment is, beside the treatment of actual medical problems, to avoid side effects such as injuries to healthy tissue. In the case of dental treatment using laser beams the tooth is subject to heat caused by energy transfer, whereby healthy tooth material adjoining the carious regions, and the tooth pulp with its associated nerve endings in particular, is affected. If inflammatory processes occur, pain attacks can be initiated at pulp temperatures as low as 37° C. and irreversible damage be caused by long-term thermal stressing up to and including complete loss of vitality of the treated tooth.

Despite the use of cooling media, in particular cooling liquids or cooling air, sufficient cooling of the healthy tooth tissue surrounding the treatment area is not fully guaranteed. In order to avoid damage to the healthy tooth tissue a device and a method for monitoring the tooth temperature is disclosed in EP 941 707 A2, which allow use of the operating parameters of the laser, the treatment duration and information on the tooth to be treated to calculate the temperature prevalent in the tooth. The disadvantage of this device is that determination of the tooth temperature is performed solely by means of the calculations carried out by the control unit, based in part on the values entered before treatment commences, and therefore does not reflect the actual treatment situation at the tooth. The calculated values therefore provide the user only with an approximate estimate of the temperature conditions at the tooth. Moreover, the input of parameters before each treatment is time-consuming for the user.

The present invention therefore has the aim of providing a device for emitting a laser beam for dental treatment with an improved determination of the tooth temperature.

SUMMARY

Disclosed below are representative embodiments that are not intended to be limiting in any way. Instead, the present disclosure is directed toward novel and nonobvious features, aspects, and equivalents of the embodiments of the wire strapper dispenser for use with a press and methods described below. The disclosed features and aspects of the embodiments can be used alone or in various novel and nonobvious combinations and sub-combinations with one another.

The invented handpiece, which can be executed as a straight or contra-angle handpiece with an angled head, depending on the application, or the invented coupling, are equipped with a temperature sensor, e.g., an infra-red sensor, which measures the intensity of the heat radiation emitted by the tooth and in particular by the tissue around the treatment area (and thus the temperature of the tissue around the treatment area). The heat radiation emitted by the tooth is in the wavelength range greater than 5.0 µm and is thus sufficiently differentiated from the wavelength of the laser beam, which does not exceed 3.5 µm. Preferentially, therefore, a temperature sensor with a measuring range not below 5.0 µm is used, ensuring that the temperature sensor does not react to the laser beam. Alternatively, the temperature sensor can be fitted with a filter, preferably a spectral filter, which filters out wavelengths smaller than 5.0 µm.

In a first embodiment the temperature sensor is fitted to the outside of the handpiece, preferably on the outer perimeter of the distal end of the handpiece in the immediate vicinity of the orifice for emitting the laser beam. In accordance with a second preferred embodiment, the temperature sensor is located inside the handpiece, in particular in the optical path of the laser light or inside the coupling, allowing better protection from soiling and damage.

If the temperature sensor is located inside part of the handpiece/coupling in particular, which is held in the hand by the user for a prolonged period, there is a danger of the body heat of the user warming the hand grip sleeve and the radiation of the hand grip sleeve subsequently influencing and falsifying the measurement of the heat radiation. The handpiece and/or the coupling is therefore preferably equipped with an inner sleeve located inside the hand grip sleeve and connected to fixed components within the handpiece. A gap between the hand grip and the inner sleeve serves as an insulator. In addition, the gap between the two sleeves can be connected to a rotor wheel, preferably located in the control unit, which forces cooling air into the gap by means of a supply tube. The heat is convectively transported from the handpiece with the cooling air by means of an opening in the proximal area of the handpiece/coupling or via a return air line in the supply tube and the radiation of the hand grip sleeve thus reduced.

Additional protection from the radiation of the hand grip sleeve is achieved by casing the temperature sensor, preferably in a metallic encapsulation, with a window of zinc selenide or germanium to allow passage of the heat radiation and a bore for the signal wire, sealed from the interior of the handpiece by a seal, preferably an O-ring. This also protects the temperature sensor from direct contact with vapours or chemicals during cleaning or disinfection.

Determination of the temperature at the treatment location is limited to a relatively small range between approximately 37° C. (body temperature of a healthy human) and approximately 43° C. (thermal stimulus threshold of the nerves in the pulp). The thermal wavelengths corresponding to this temperature range are thus situated approximately in the range of about 9.0 to about 9.4 µm. It follows that in a preferred embodiment the detection range of the temperature sensor may be limited to a range of about 9.0 to about 9.4 µm, in particular a range of about 9.10 to about 9.35 µm, or the temperature sensor be fitted with a filter which separates out the wavelengths outside of this range.

With the help of the procedure for controlling the power output of a laser source in a device for emitting a laser beam for dental treatment and the process steps:
  emission of a laser beam to a treatment area,
  measurement of at least part of the heat radiation emitted from the treatment area by means of a temperature sensor, preferably with an infra-red sensor,
  emission of a signal by the temperature sensor proportional to the intensity of the heat radiation,
  guidance of the signal to and processing by the evaluation and control electronics,
  interruption of emission of the laser beam to the treatment area or reduction of power output of the laser source the chance overheating and damage of the healthy tooth tissue and the pulp neighbouring the treatment area is reduced during treatment.

The process for warning a user about the reaching or exceeding a given temperature threshold during dental treatment with the process steps:
- emission of a laser beam to a treatment area,
- measurement of at least part of the heat radiation emitted from the treatment area by means of a temperature sensor, preferably with an infra-red sensor,
- emission of a signal by the temperature sensor proportional to the intensity of the heat radiation,
- guidance of the signal to and processing by the evaluation and control electronics,
- generation and emission of an acoustic or visual signal when reaching or exceeding the temperature threshold by an electrical acoustic or light element connected to the electronics, preferably a LED, provides immediate alarming of the user if critical temperature ranges are reached or exceeded. Preferably, when reaching or exceeding the temperature threshold, the emission of the laser beam to the treatment area is interrupted or the power output of the laser source reduced.

A procedure for intermittent emission of a laser beam and measurement of the heat radiation with the process steps:
- emission of a laser beam to a treatment area,
- interruption of the laser beam emission
- measurement of at least part of the heat radiation emitted from the treatment area by means of a temperature sensor, preferably with an infra-red sensor,
- emission of a signal by the temperature sensor proportional to the intensity of the heat radiation,
- guidance of the signal to and processing by the evaluation and control electronics,
- renewed emission of the laser beam to a treatment area if the given temperature threshold is not reached or exceeded reduces the danger of influencing detection of heat radiation by the temperature sensor, in particular for laser sources that emit long wave radiation, e.g. $CO_2$ lasers. Preferably, when reaching or exceeding the temperature threshold, the emission of the laser beam to the treatment area is again interrupted or the power output of the laser source reduced or an acoustic or visual signal generated and emitted.

The invention is described below based on preferred embodiments and with reference to the drawings provided.

DETAILED DESCRIPTION OF THE PREFERRED EMBODIMENTS

Figure 1:
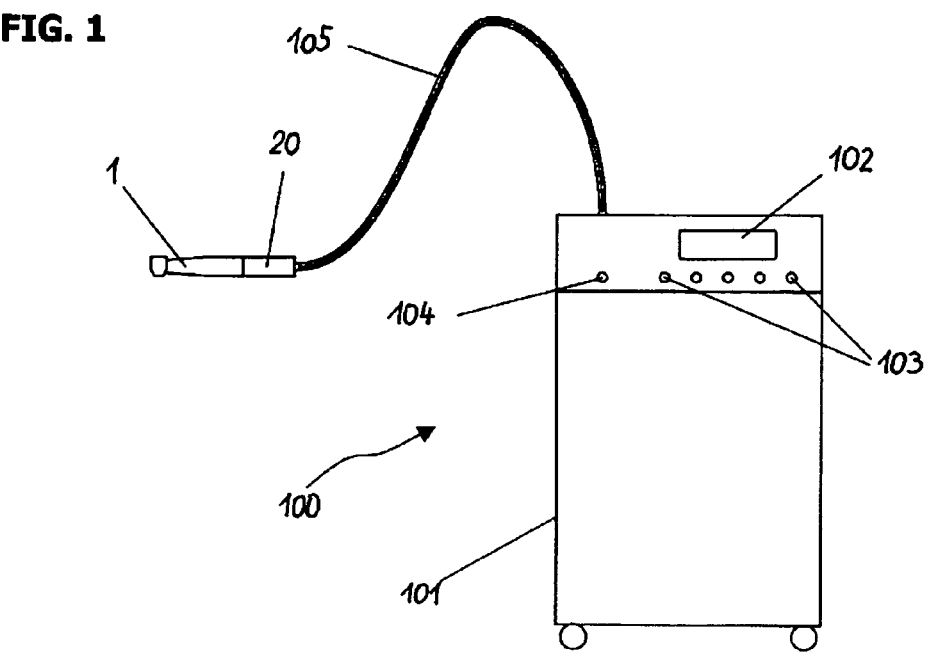
FIG. 1 shows the invented device for emitting a laser beam for dental treatment.

The invented device 100 for emitting a laser beam for dental treatment in accordance with FIG. 1 consists of a casing 101, containing the laser source and a control device with evaluation and control electronics, preferably as part of a microprocessor. The electronics serve as open and closed loop controls for the operating parameters, for example the power output of the laser source or volume control of the cooling media water and air, and for processing the signals from the sensors, which are connected to the handpiece 1 or the coupling 20. On the display 102, which is connected to the electronics, the user can read off operating data and select programmes or alter parameters with the help of a numbers of push buttons 103. Via an interface 104 the evaluation and control electronics are connected to a printer for output of the operating settings and treatment parameters. Preset operating programs and editable settings and parameters are stored in one or more memories connected to the electronics or can be accessed from there. A supply tube 105 containing lines for cooling liquid, cooling air, a fibre optic cable for the laser beam and further lines for signal transmission and electricity supply to illumination elements connects the coupling and the handpiece 1 to the laser source and electronics within casing 101 and the connections for the external sources of electricity, compressed air and liquids. Of course, instead of the supply tube 105 an articulated mirror arm may be used to transmit the laser beam. The laser source can be any source emitting a laser beam in the wavelength range from about 400 nm to about 3.5 μm, in particular from about 700 nm to about 1.064 nm.

Figure 2:
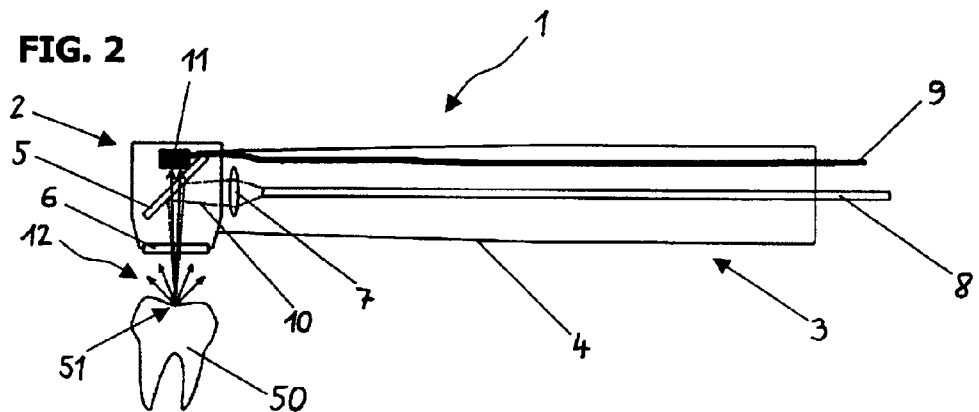
FIG. 2 shows a first embodiment of the invented handpiece.

The invented handpiece 1 shown in FIG. 2 is designed as a contra angle handpiece with a hand grip 3 and an angled head 2. By means of the fibre optic cable 8, which protrudes into the handgrip sleeve 4 of the handpiece 1, the laser beam 10 is transmitted into the distal area of handgrip section 3, where it exits the fibre optic cable 8. After passing through an optical element, for example a convex lens 7, the laser beam 10 is deflected towards the exit aperture 6 in the head 2 of the handpiece 1 by a mirror 5 in the head, exits the handpiece 1 through the exit aperture 6 and is projected onto the treatment area 51 of the tooth 50. In order to avoid ingress of particles (ablated tissue, cooling liquid, etc.) into the handpiece 1 thus causing soiling of the mirror 5 in particular and other optical elements 7, a protective glass can be fitted to the exit aperture 6. The protective glass is preferably designed as a lens or with a refraction index which is variable across the cross-section for conditioning the passing beam 10, 12.

The energy transferred by the laser beam 10 leads to warming of the tooth 50 and the tissue surrounding the treatment area 51 in particular. Part of this energy is emitted by the tooth 50 as heat radiation 12 (infra-red radiation in particular at a wavelength greater than 5.0 μm) to a half-space. At least part of this heat radiation 12 enters the handpiece 1 through the exit aperture 6 and can here be detected by a temperature sensor 11, in particular an infra-red sensor for wavelengths greater than 5.0 μm, preferably an infra-red sensor for wavelengths in the range of about 9.0 μm to about 9.4 μm, most preferably in the range of about 9.10 μm to about 9.35 μm. The temperature sensor 11 generates a signal corresponding to the intensity of the heat radiation 12 (and thus the temperature of the tissue surrounding the treatment area 51), which is transmitted to the evaluation and control electronics 15, which are formed as part of the handpiece 1 (see FIG. 4), the coupling 20 or the device 100, via a signal wire 9. The evaluation and control electronics, preferably forming an integral part of the microprocessor in the device 100, receive, process and compare the signals to a preset temperature threshold and interrupts the laser beam 10 to the treatment area if the temperature threshold is reached or exceeded, preferably by closing a shutter in the path of the laser beam 10. Alternatively, the power output of the laser source can be reduced or the user be made aware of exceeding the threshold value by an acoustic or visual signal, for example by illumination of a warning light.

The temperature threshold (or a temperature range) is stored in a memory connected to the electronics. It is entered by the handpiece 1 or device 100 manufacturer. However, the user can preferably edit the temperature threshold via the push buttons 103 (FIG. 1) and thus take special treatment requirements into consideration, e.g. for an already inflamed tooth, by reducing the threshold value.

In accordance with FIG. 2, the temperature sensor 11 is located in the head 2 of the handpiece 1, allowing favourable proximity of the temperature sensor 11 to the treatment area 51 and thus to the source of the heat radiation 12. The temperature sensor 11 is preferably located behind the mirror 5 and thus outside of the optical path of the laser beam 10. The mirror 5 is designed as a semi-transparent mirror which reflects wavelengths below 3.5 µm, preferably below 1.1 µm, i.e. the laser beam 10 or plasma radiation occurring as a result of the treatment of the tooth and which is transmitted for evaluation to an evaluation device forming part of the laser treatment device, and which is transparent to wavelengths above 5.0 µm, preferably between about 9.0 to about 9.4 µm, most preferably between about 9.10 to about 9.35 µm, i.e. heat radiation 12.

If it is not possible, for example due to space considerations, to locate the temperature sensor 11 in the head 2 of the handpiece 1, the temperature sensor 11 may be located in the grip 3. The temperature sensor 11 is preferably arranged between the distal opening 6 and the nearest optical element for the laser beam, for example a lens 7 or a scanner, in order to ensure that the properties of the optical element (and any following optical elements), for example transmission or reflection properties, only need be optimised for the laser beam 10.

Figure 4:
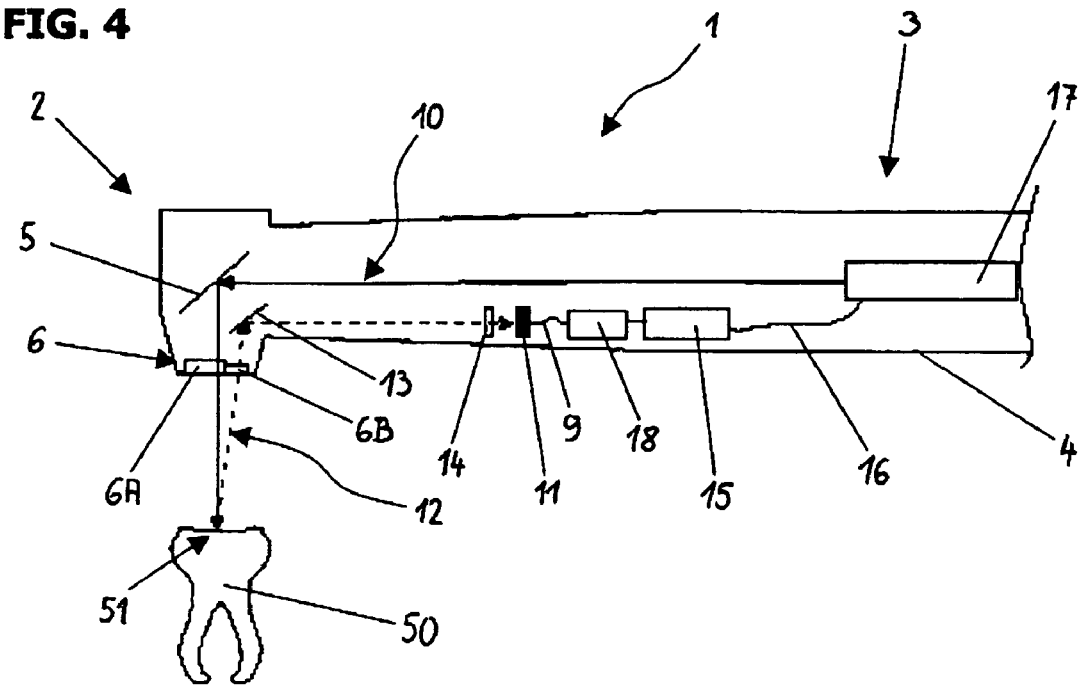
FIG. 4 shows a second embodiment of the invented handpiece.

FIG. 4 shows an embodiment in which the temperature sensor 11 is located in the optical path of the laser beam 10 in the grip 3. For the term optical path we understand the cavity for passage of the fibre optic cable 8 or the free laser beam 10 in the handpiece 1. In contrast to FIG. 2, the laser source 17 here is located in the handpiece 1, making a fibre optic cable 8 for transmitting the laser beam 10 redundant. A two-part protective glass cover 6A, 6B is fitted to the exit aperture 6, whereby the two protective glasses 6A, 6B possess different properties for preparing the different types of radiation, preferably different focal lengths or different refraction indices, or the glasses 6A, 6B are manufactured from different materials. Of course, instead of a two- or more part protective glass a one-piece glass can also be used, divided into two or more areas of differing properties. The properties of protective glass 6A are optimised for the laser beam 10, which preferably passes through protective glass 6A. It is preferably manufactured from quartz glass and in designed as a convex lens, which bundles the laser beam 10 passing out through the handpiece 1. Protective glass 6B is preferably manufactured from zinc selenide or germanium and also designed as a convex lens, but intended to bundle the heat radiation 12 for transfer into the handpiece 1.

By means of a mirror 13 the heat radiation 12 advances further to one or more filters 14, whereby the filter 14 is either a resonator (Etalon), transmission filter, refraction filter (prism) or diffraction filter (grid). The filter 14 filters wavelengths smaller than 5.0 µm, preferably outside of the range of about 9.0 to about 9.4 µm, in particular of about 9.10 to about 9.35 µm. The filtered heat radiation 12 finally arrives at the temperature sensor 11, which sends a signal corresponding to the intensity of the heat radiation 12 along the signal wire 9 to an amplifier 18 located in the grip 3 and further to the evaluation and control electronics 15 located on a circuit board. The electronics 15 are connected to the laser source 17 by a further signal wire 16 which affects an interruption of the laser beam 10, or a reduction in the power output of the laser source 17, if a temperature threshold is reached or exceeded. Of course, further optical elements for preparing the heat radiation 12 may be located between the mirror 13 and the temperature sensor 11, for example lenses. An additional digitisation unit (analogue-digital converter) can be connected to the temperature sensor 11 to convert the analogue signal of the temperature sensor 11 to a digital signal, making the signal transmission independent of the current strength.

Figure 3:
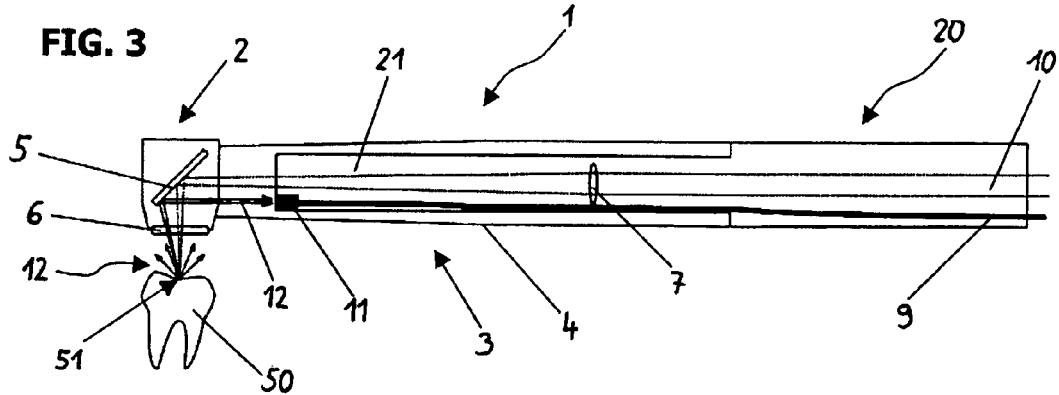
FIG. 3 shows an embodiment of the invented coupling with a handpiece.

FIG. 3 shows the invented coupling 20 connected to the handpiece 1, which serves as a connector between the handpiece 1 and the supply tube 105 (FIG. 1). The coupling 20 is preferably implemented as a rotary coupling, enabling the user to rotate the handpiece 1 against the coupling 20 and the neighbouring components during treatment. The laser beam 10 is transferred to the mirror 5 via the optical path in the coupling 20, by means of optical elements, for example a lens 7, through the optical path in the coupling tube 21 and the distal end of the grip 3. The heat radiation 12 emitted by the treatment area 51 is also deflected by the mirror 5 into the optical path of the laser beam 10. The wide reflection range (about 400 nm to about 10.60 µm) of the mirror 5 is preferably achieved by providing multiple coatings of the mirror surface to facilitate selective reflection of certain wavelength ranges. Alternatively, a purely metal mirror can be employed.

The temperature sensor 11 for measuring the heat radiation 12 is fitted to the coupling tube 21, preferably in the optical path of the laser beam 10. Favourable for this arrangement is that by freeing the handpiece 1 from the coupling 20, the temperature sensor 11 can be removed from the handpiece 1 and the handpiece 1 thus be sterilised without further problems. This is particularly important for applications involving the removal of tissue and simultaneous use of cooling media, in particular cooling liquids, as the danger of particles and pathogens entering the handpiece 1 on droplets of liquid is particularly great and can lead to cross-contamination between patients. Also, with the temperature sensor 11 located on the coupling 20, no contacts, for example sliding contacts and sliprings, are required to transfer the signals across the handpiece 1/coupling 20 interface. The transmission and evaluation of the signal from the temperature sensor 11 corresponds to the description to FIGS. 2 and 4. To avoid repetition, this will not be dealt with further here.

The length of the coupling tube 21 is preferably dimensioned such that the distal end of the coupling tube 21 reaches close to the head 2 of the handpiece 1 and the temperature sensor 11 is located in the distal area of the coupling tube 21. This, in turn, allows close proximity of the temperature sensor 11 to the treatment area 51 and thus to the source of the heat radiation 12, which results in a reduction in attenuation and scattering of the heat radiation 12 with increasing distance.

Figure 5:
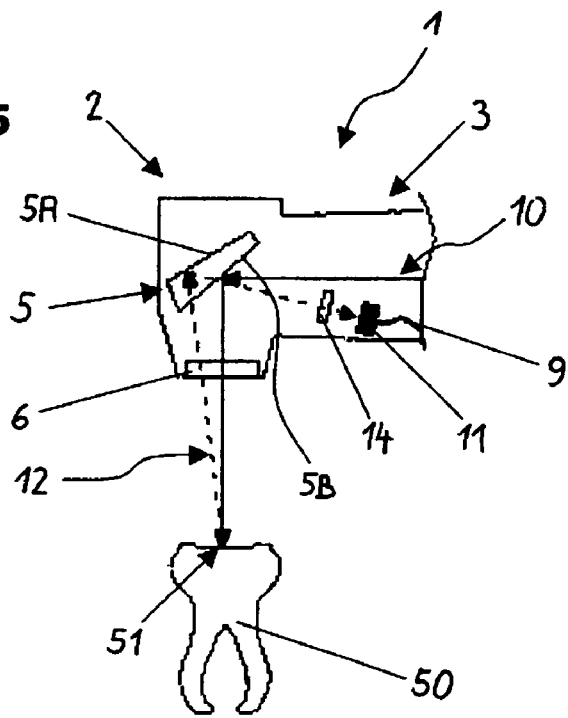
FIG. 5 shows a third embodiment of the invented handpiece.

In place of the two mirrors 5, 13, only one mirror 5 is used in the handpiece 1 shown in FIG. 5. The mirror 5 has a front surface 5B (i.e. a side close to the laser source) and a rear surface 5A (i.e. a side further away from the laser source). Both sides 5A, 5B are coated with different materials, such that only one of the two types of radiation 10, 12 is selectively reflected respectively by one of the two sides 5A, 5B. In FIG. 5, for example, the front surface 5B reflects radiation below about 3.5 µm (laser beam 10) and allows radiation above about 5.0 µm (heat radiation 12) to pass, which is then reflected by the rear surface 5A. In this way it is possible to achieve beam separation and heat radiation 12 is deflected to temperature sensor 11 located in the side of the optical path of the laser beam 10. To amplify the deflection the two reflecting sides 5A, 5B are arranged approximately antiparallel.

The invention is not restricted to the described embodiments, but encompasses all possible embodiments that do not alter the basic design principle of the invention and analogous functions.

We claim:

1. A device for emitting a laser beam for dental treatment with a laser source, the device comprising a coupling, a handpiece, an optical path for transmitting the laser beam from the laser source to the coupling and to the handpiece, and a temperature sensor for detecting heat radiation emitted by a treated tooth, wherein the handpiece comprises an exit aperture through which the laser beam is directed toward the treated tooth, wherein the coupling is detachable from the handpiece, wherein the coupling is positioned between the exit aperture of the handpiece and the laser source and wherein the temperature sensor is located on a distal end of the coupling or on a coupling tube of the detachable coupling.

2. The device of claim 1, wherein the temperature sensor comprises an infrared sensor.

3. The device according to claim 1, wherein the temperature sensor is located inside the handpiece when the coupling is coupled to the handpiece.

4. The device according to claim 1, wherein if the temperature sensor is located on the coupling tube, the temperature sensor is located inside the coupling.

5. The device according to claim 1, wherein the temperature sensor is located on the coupling.

6. The device according to claim 1, wherein the temperature sensor is located in the optical path of the laser beam.

7. The device according to claim 1, wherein the temperature sensor is located between the exit aperture of the handpiece and a nearest optical element for the laser beam.

8. The device according to claim 1, wherein the handpiece comprises an angled head, in which is located a mirror to deflect at least the laser beam, and the mirror having a reflection range of approximately 400 nm to approximately 10.60 µm for reflecting the heat radiation emitted by the treated tooth to the temperature sensor.

9. The device according to claim 1, comprising an evaluation and control circuit, which receives signals from the temperature sensor, processes the signals and, if a preset temperature threshold is exceeded, interrupts the laser beam to a treatment area or reduces a power output of the laser source or reports a violation of the threshold value to a user through an acoustic or visual signal.

10. The device according to claim 9, wherein the evaluation and control circuit is connected to one or more of a display, an interface for a printer, and a storage system for visualizing, printing or storing, respectively, one or more temperature values per treatment in numerical form or graphical form, or numerical form and graphical form.

11. The device according to claim 1, comprising a protective glass in a distal opening of the handpiece, whereby the protective glass is designed as a lens or as a protective glass with a variable refraction index across at least one cross-section.

12. The device according to claim 1, wherein the temperature sensor detects wavelengths greater than 5.0 µm.

13. The device according to claim 1, wherein the temperature sensor detects wavelengths in a range from about 9.0 µm to about 9.4 µm or in a range from about 9.10 µm to about 9.35 µm.

14. The device according to claim 1, wherein the temperature sensor is connected to a digitization unit, which converts an analog signal of the temperature sensor into a digital signal.

15. The device according to claim 1, comprising an inner sleeve in the coupling, which is separated by a gap from a grip sleeve, for shielding the temperature sensor from heat radiation across the grip sleeve.

16. The device according to claim 1, wherein the temperature sensor is encased in a capsule with a zinc selenide or germanium window.

17. The device according to claim 1, wherein the temperature sensor is located on the coupling tube.

18. The device according to claim 17, wherein a length of the coupling tube is dimensioned such that a distal end of the coupling tube reaches close to a head of the handpiece and the temperature sensor is located at the distal end of the coupling tube.

19. The device according to claim 1, wherein the coupling comprises a rotary coupling for rotating the handpiece against the coupling.

20. The device according to claim 1, wherein the temperature sensor is positioned such that it remains spaced from the treated tooth during dental treatment.

21. The device according to claim 1, wherein the temperature sensor is positioned such that it remains uncontaminated during dental treatment.

22. The device according to claim 1, wherein the coupling tube is releasably accommodated in a receptacle of the handpiece.

* * * * *